(12) United States Patent
Ransbury et al.

(10) Patent No.: US 8,311,633 B2
(45) Date of Patent: Nov. 13, 2012

(54) INTRAVASCULAR IMPLANTABLE DEVICE HAVING SUPERIOR ANCHORING ARRANGEMENT

(75) Inventors: Terrance Ransbury, Chapel Hill, NC (US); Kevin Holbrook, Chapel Hill, NC (US)

(73) Assignee: Synecor LLC, Chapel Hill, NC (US)

( * ) Notice: Subject to any disclaimer, the term of this patent is extended or adjusted under 35 U.S.C. 154(b) by 1278 days.

(21) Appl. No.: 11/999,519

(22) Filed: Dec. 4, 2007

(65) Prior Publication Data

US 2008/0167702 A1    Jul. 10, 2008

Related U.S. Application Data

(60) Provisional application No. 60/868,434, filed on Dec. 4, 2006, provisional application No. 60/868,437, filed on Dec. 4, 2006.

(51) Int. Cl.
  *A61N 1/372* (2006.01)
(52) U.S. Cl. .......................................................... 607/36
(58) Field of Classification Search .......... 607/115–116, 607/122, 126, 130, 36
  See application file for complete search history.

(56) References Cited

U.S. PATENT DOCUMENTS

| | | |
|---|---|---|
| 3,835,864 A | 9/1974 | Rasor et al. |
| RE30,366 E | 8/1980 | Rasor et al. |
| 5,170,802 A | 12/1992 | Mehra |
| 5,405,363 A | 4/1995 | Kroll et al. |
| 5,487,760 A | 1/1996 | Villafana |
| 5,509,411 A | 4/1996 | Littmann et al. |
| 5,531,779 A | 7/1996 | Dahl et al. |
| 5,843,132 A | 12/1998 | Ilvento |
| 6,141,576 A | 10/2000 | Littmann et al. |
| 6,141,588 A | 10/2000 | Cox et al. |
| 6,360,130 B1 | 3/2002 | Duysens et al. |
| 6,442,413 B1 | 8/2002 | Silver |
| 6,445,953 B1 | 9/2002 | Bulkes et al. |
| 6,613,076 B1 | 9/2003 | Cherif-Cheikh |
| 6,950,705 B2 | 9/2005 | Bardy et al. |
| 7,072,171 B1 | 7/2006 | Muffoletto et al. |
| 7,082,336 B2 | 7/2006 | Ransbury et al. |
| 7,101,642 B2 | 9/2006 | Tsukamoto et al. |

(Continued)

FOREIGN PATENT DOCUMENTS

WO    WO 00/74557 A1    12/2000

(Continued)

OTHER PUBLICATIONS

International Preliminary Report on Patentability (PCT/US2007/024912), dated Jun. 18, 2009.

(Continued)

*Primary Examiner* — Carl H Layno
*Assistant Examiner* — Jessica Sarcione

(57) ABSTRACT

Anchoring methods, systems and devices anchor an intravascular implantable device within a vessel that is located superior to the heart, i.e. above the heart in a direction toward the head of a patient. A method of providing an intravascular device and instructions for implanting the intravascular device, includes providing an intravascular device having an elongate device body with a proximal end and a distal end that is adapted for chronic implantation within the vasculature of a patient and that includes a distal portion of the intravascular device proximate the distal end of the elongate device body, and providing instructions for chronically implanting the intravascular device substantially wholly within the vasculature of a patient in a target vessel superior to the heart of the patient.

12 Claims, 14 Drawing Sheets

U.S. PATENT DOCUMENTS

| | | | |
|---|---|---|---|
| 7,120,495 B2 | 10/2006 | Bardy et al. | |
| 7,239,921 B2 | 7/2007 | Canfield et al. | |
| 7,363,082 B2 | 4/2008 | Ransbury et al. | |
| 7,519,424 B2 | 4/2009 | Dennis et al. | |
| 7,529,586 B2 | 5/2009 | Wahlstrand et al. | |
| 7,529,589 B2 | 5/2009 | Williams et al. | |
| 7,616,992 B2 | 11/2009 | Dennis et al. | |
| 7,617,007 B2 | 11/2009 | Williams et al. | |
| 7,627,376 B2 | 12/2009 | Dennis et al. | |
| 7,734,343 B2 | 6/2010 | Ransbury et al. | |
| 7,747,335 B2 | 6/2010 | Williams | |
| 7,840,282 B2 | 11/2010 | Williams et al. | |
| 2001/0044568 A1 | 11/2001 | Langberg et al. | |
| 2002/0143379 A1 | 10/2002 | Morgan et al. | |
| 2003/0109914 A1 | 6/2003 | Westlund et al. | |
| 2004/0116992 A1 | 6/2004 | Wardle et al. | |
| 2004/0138744 A1 | 7/2004 | Lashinski et al. | |
| 2004/0249431 A1* | 12/2004 | Ransbury et al. | 607/126 |
| 2005/0016109 A1 | 1/2005 | Rouse | |
| 2005/0043765 A1 | 2/2005 | Williams et al. | |
| 2005/0080472 A1* | 4/2005 | Atkinson et al. | 607/126 |
| 2005/0154437 A1 | 7/2005 | Williams | |
| 2005/0165456 A1 | 7/2005 | Mann et al. | |
| 2005/0222678 A1 | 10/2005 | Lashinski et al. | |
| 2005/0228471 A1* | 10/2005 | Williams et al. | 607/126 |
| 2005/0234431 A1* | 10/2005 | Williams et al. | 604/890.1 |
| 2005/0273138 A1 | 12/2005 | To et al. | |
| 2006/0095078 A1 | 5/2006 | Tronnes | |
| 2006/0161166 A1 | 7/2006 | Johnson et al. | |
| 2006/0168791 A1 | 8/2006 | Richter et al. | |
| 2006/0217779 A1 | 9/2006 | Ransbury et al. | |
| 2007/0043414 A1 | 2/2007 | Fifer et al. | |
| 2007/0179550 A1 | 8/2007 | Dennis et al. | |
| 2007/0179581 A1 | 8/2007 | Dennis et al. | |
| 2007/0179583 A1 | 8/2007 | Goetzinger et al. | |
| 2007/0265673 A1 | 11/2007 | Ransbury et al. | |
| 2008/0058886 A1 | 3/2008 | Williams | |
| 2008/0147168 A1 | 6/2008 | Ransbury et al. | |
| 2008/0154327 A1 | 6/2008 | Ransbury et al. | |
| 2009/0198295 A1 | 8/2009 | Dennis et al. | |
| 2011/0032387 A1 | 2/2011 | Takahashi | |
| 2011/0054555 A1 | 3/2011 | Williams et al. | |
| 2011/0071585 A1* | 3/2011 | Ransbury et al. | 607/4 |

FOREIGN PATENT DOCUMENTS

| | | |
|---|---|---|
| WO | WO 2008/070120 A2 | 6/2008 |
| WO | WO 2010/144916 A2 | 12/2010 |

OTHER PUBLICATIONS

International Search Report and the Written Opinion of the International Searching Authority (PCT/US2007/024912), dated Jun. 5, 2008.

International Search Report and Written Opinion (PCT/US2008/085448) dated, Jun. 18, 2009.

International Preliminary Report on Patentability (PCT/US2008/085448) dated, Jun. 17, 2010.

Application and File history for U.S. Appl. No. 12/815,210, filed Jun. 14, 2010. Inventor: Ransbury.

Application and File history for U.S. Appl. No. 12/957,969, filed Dec. 1, 2010. Inventors: Ransbury et al.

Application and File history for U.S. Appl. No. 11/999,517, filed Dec. 4, 2007. Inventors: Ransbury et al.

Application and File history for U.S. Appl. No. 12/815,355, filed Jun. 14, 2010. Inventor: Ransbury.

International Search Report (PCT/US2010/038544), dated Feb. 25, 2011.

* cited by examiner

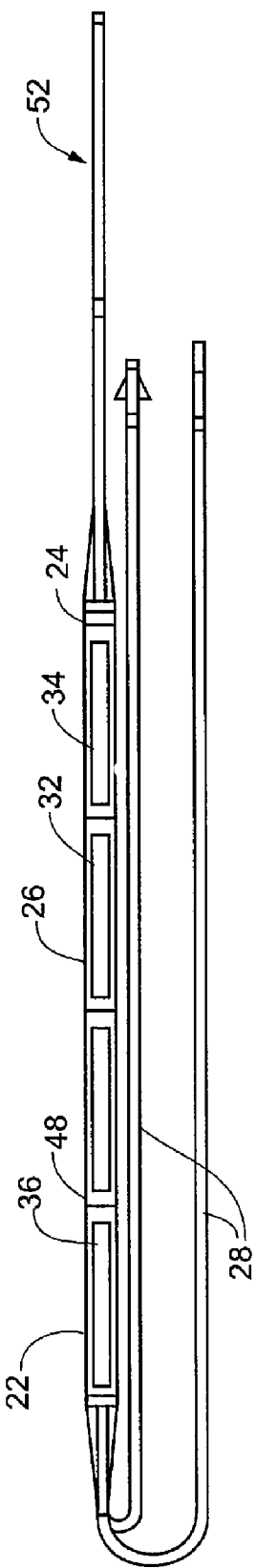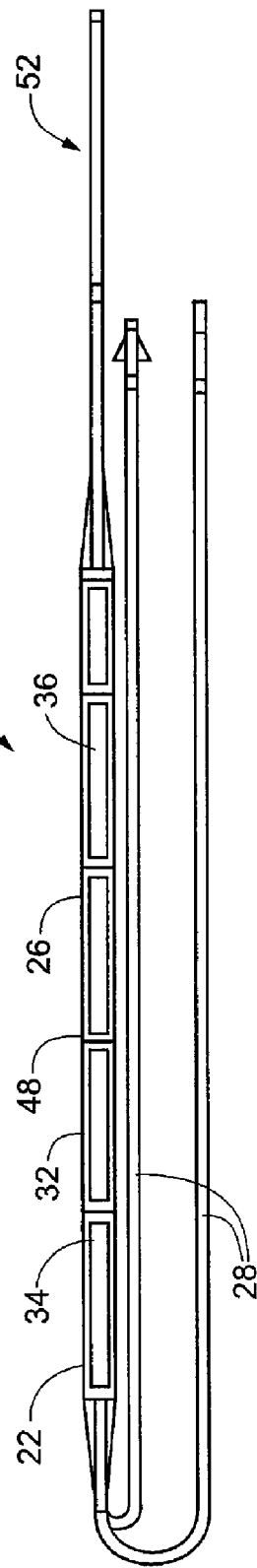

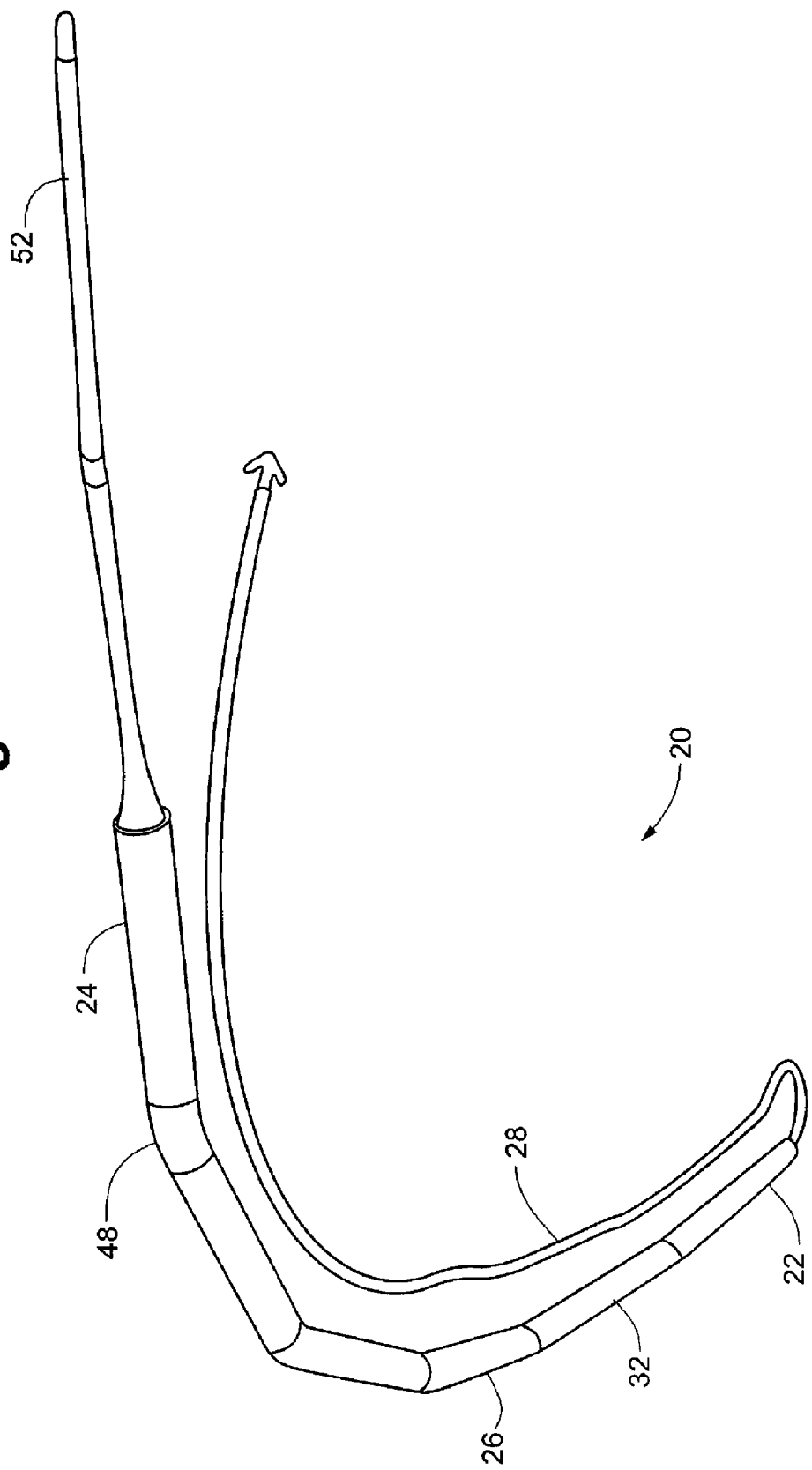

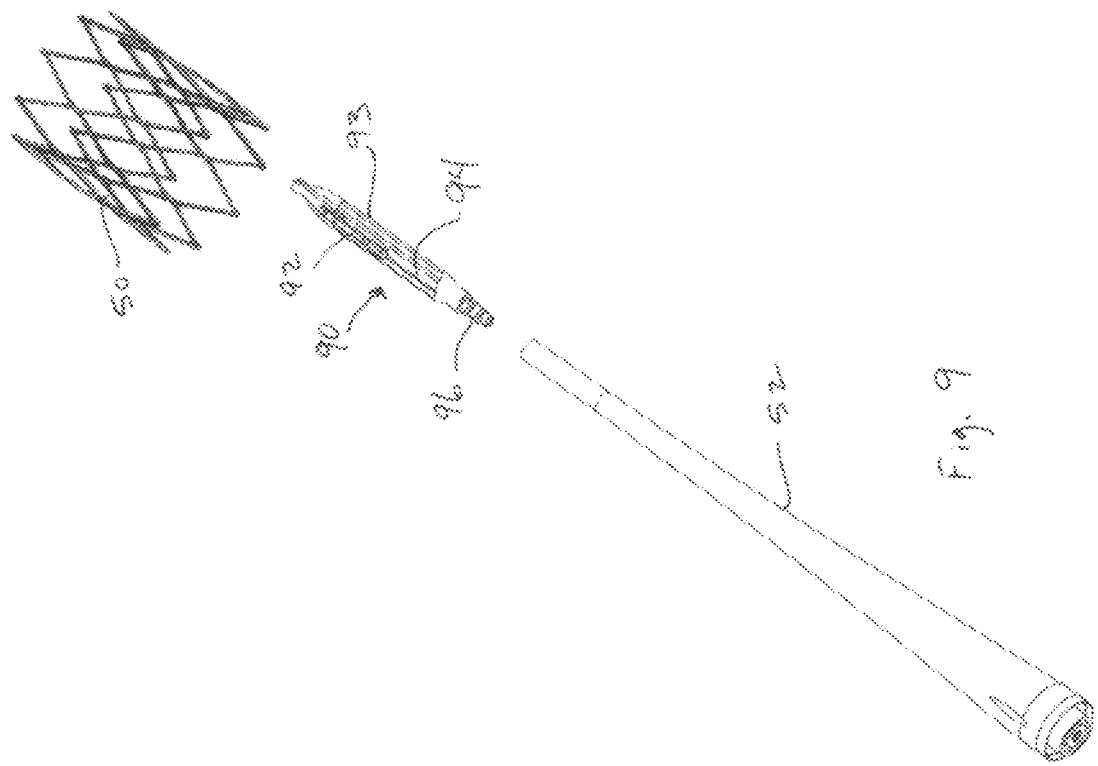
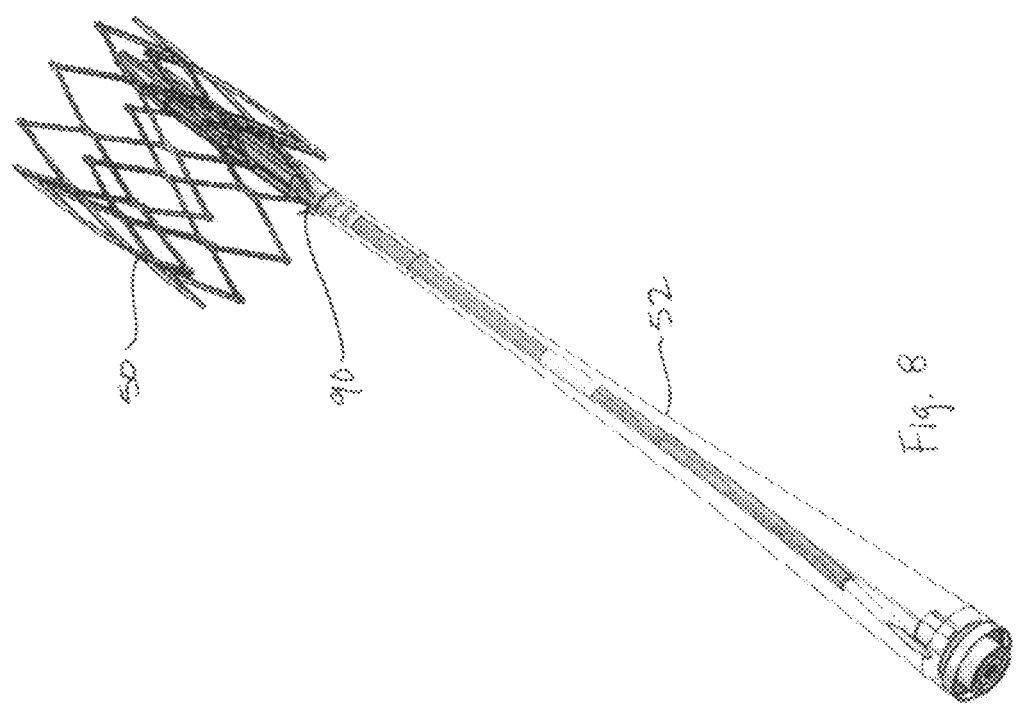

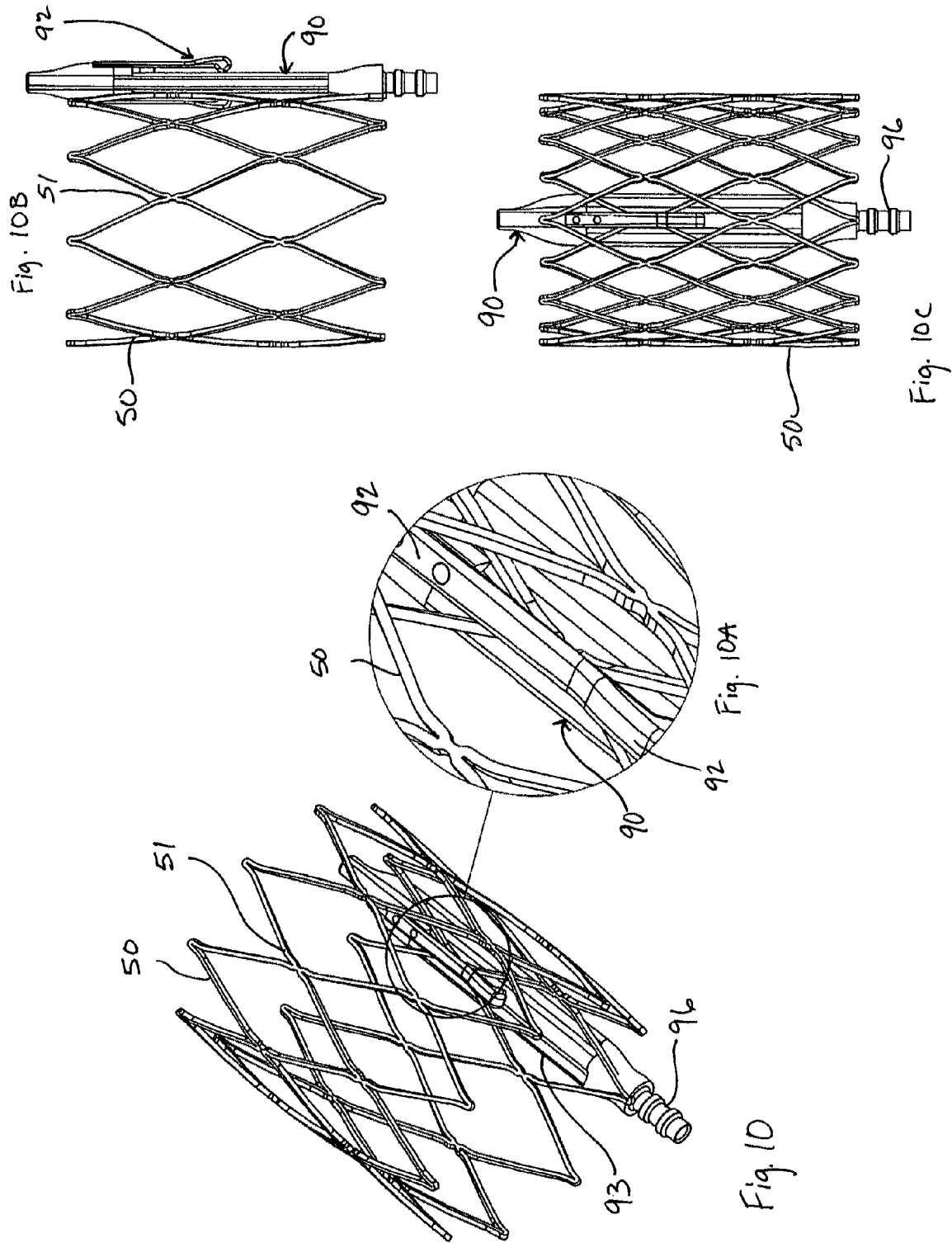

INTRAVASCULAR IMPLANTABLE DEVICE HAVING SUPERIOR ANCHORING ARRANGEMENT

RELATED APPLICATIONS

The present application claims the benefit of U.S. Provisional Application No. 60/868,434, filed Dec. 4, 2006, and U.S. Provisional Application No. 60/868,437, filed Dec. 4, 2006, and U.S. Provisional Application titled "Implantation Methods, Systems and Tools for Intravascular Implantable Devices", filed Dec. 3, 2007, the disclosures of which are hereby incorporated by reference in their entireties.

FIELD OF THE INVENTION

The present invention relates generally to surgical devices and methods for retaining medical devices within the body, and more specifically to a method and system for anchoring an intravascular implantable device within a vessel that is located superior to the heart.

BACKGROUND OF THE INVENTION

Implantable medical devices such as pacemakers, defibrillators, and implantable cardioverter defibrillators ("ICDs") have been successfully implanted in patients for years for treatment of heart rhythm conditions. Pacemakers are implanted to detect periods of bradycardia and deliver low energy electrical stimuli to increase the heart rate. ICDs are implanted in patients to cardiovert or defibrillate the heart by delivering high energy electrical stimuli to slow or reset the heart rate in the event a ventricular tachycardia (VT) or ventricular fibrillation (VF) is detected. Another type of implantable device detects an atrial fibrillation (AF) episode and delivers electrical stimuli to the atria to restore electrical coordination between the upper and lower chambers of the heart. Still another type of implantable device stores and delivers drug ad/or gene therapies to treat a variety of conditions, including cardiac arrhythmias. The current generation for all of these implantable devices are typically can-shaped devices implanted under the skin that deliver therapy via leads that are implanted in the heart via the patient's vascular system.

Next generation implantable medical devices may take the form of elongated intravascular devices that are implanted within the patient's vascular system, instead of under the skin. Examples of these intravascular implantable devices are described, for example, in U.S. Pat. No. 7,082,336, U.S. Published Patent Application Nos. 2005/0043765 A1, 2005/0208471A1 and 2006/0217779A1. These devices contain electric circuitry and/or electronic components that are hermetically sealed to prevent damage to the electronic components and the release of contaminants into the bloodstream. Due to the length of these implantable devices, which in some cases can be approximately 10-60 cm in length, the devices generally are designed to be flexible enough to move through the vasculature while being sufficiently rigid to protect the internal components.

The issue of how to secure such an implantable device in the vasculature is one of the challenges for this next generation of intravascular implantable devices. In addition to the mechanical and operational considerations related to an anchoring system, there are physical and biological implications for the patient, as well as considerations for how an anchoring system may affect the manner in which the implantable device delivers therapy.

As described in some of the embodiments shown in U.S. Pat. No. 7,082,336 and U.S. Published Patent Application No. 2004/0249431, the anchoring system was arranged proximate the middle of the intravascular implantable device so as to be positioned in the vena cava within the thorax. This arrangement anchored the intravascular implantable device near the middle of the patient's torso at a location generally corresponding to the diaphragm. In some embodiments, the anchoring system was integrated with the body of the intravascular implantable device. In other embodiments, the anchoring system was a separate device, such as a stent, that was used to pin the body of the intravascular implantable device in position between the stent and the vessel wall. In still other embodiments, a lead extending from a distal end of the body of the intravascular device would also be anchored in the vasculature, such as in a subclavian vein.

An alternative integrated anchoring system for an intravascular implantable device is described in some of the embodiments shown in U.S. Published Patent Application No. 2005/0208471A1. This alternative integrated anchoring system utilized a radially expandable member positioned proximate the middle of the body of the device to secure the device. In some embodiments, the radially expandable member centered the device within the diameter of the vessel. In other embodiments, two or more radially expandable members were used to secure the middle of the body of the device within a vessel.

The approaches of securing an intravascular implantable device within the thorax by an anchoring system proximate the middle of the body of the device and positioned in the vena cava generally corresponding to the diaphragm of the patient were intended to create a secure and balanced anchoring of the device within the largest diameter vessel in the body. These approaches sought to reduce issues of thrombosis and potential dislodgement of the anchoring system due to impact or movement of the patient.

While intravascular implantable devices represent a significant improvement over conventional implantable devices that are implanted subcutaneously, there are opportunities to improve and refine the designs for such intravascular devices. Accordingly, it would be desirable to provide for an improved design of an anchoring arrangement for an intravascular implantable device.

SUMMARY OF THE INVENTION

The present invention is directed to methods and systems for anchoring an intravascular implantable device within a vessel that is located superior to the heart, i.e. above the heart in a direction toward the head of a patient. In one embodiment, the present invention utilizes only a single anchoring arrangement positioned proximate a distal portion of the intravascular implantable device. In another embodiment, the present invention utilizes an anchoring arrangement that interacts with a distal portion of the intravascular implantable device that is generally smaller in cross-sectional area than a cross-sectional area of the body portion of the device. In a further embodiment, the present invention utilizes an anchoring arrangement that interacts with a distal portion of the intravascular device that is generally separable from the body portion of the device and contains no internal spaces for active components of the device.

Unlike the previous approaches to anchoring intravascular implantable devices near the middle of the patient's torso, embodiments of the present invention anchor the body portion of the intravascular implantable device in a vein that is located superior to the heart and still generally within the torso, such as the right or left cephalic veins, the right or left innominate (brachiocephalic) veins or the right or left subclavian veins. In conducting investigations with the previous approach of anchoring in the middle of the device in the thorax, the inventors of the present invention discovered that the previous anchoring arrangement generally moved in synchrony with respiration, rubbing the anchor and the intravascular implantable device against the vascular walls of the inferior vena cava and thereby causing unwanted irritation, thrombosis and/or fibrosis. Anchoring in the middle of the device also tended to constrain the movement of the device within the inferior vena cava and created more locations along the vessel for unwanted irritation, thrombosis and/or fibrosis.

In accordance with the present invention, the intravascular implantable device is anchored superior to the heart, and in one embodiment is anchored in veins that are superior to the superior vena cava and still within the torso of the body, such as the cephalic vein, the innominate vein and the subclavian vein. The intravascular implantable device may be any one or a combination of defibrillator, cardioverter, pacemaker, monitor or drug/gene therapy delivery device and may be either a temporary or permanent device.

In one embodiment, the tether portion of the implantable device extends across the sub-clavicle crush zone and the anchor is located peripheral of the sub-clavicle crush zone. The distal portion of the body of the device is proximate, but generally does not extend into, the subclavian crush zone. In this way, the anchor is located superior to the heart and in a manner so as to minimize interference with the patient's muscular-skeletal anatomy.

In one embodiment, the present invention solves the problems of previously utilized anchor locations by providing a tether portion at a distal portion of the body of the implantable device. In one embodiment, the tether portion is anchored into the vasculature superior to the heart with a conventional stent. In one embodiment, the vascular anchor is preferably separate from the implantable device and captures a tether portion that extends from the implantable device between the anchor and the vasculature. Alternatively, the anchor may be incorporated as part of the implantable device. In one embodiment, the vascular anchor and/or the tether portion of the implantable device include mechanisms to optimize interference between the anchor and the tether portion in a manner that does not induce a rupture of the vessel while providing for adequate clinical attachment of the implantable device within the patient.

In one embodiment, the anchoring of the present invention at the distal portion of the body of the intravascular implantable device permits the main body portion and proximal body portions of the device to more effectively float in the bloodstream, thereby reducing the risk of thrombosis for those portions, as well as reducing the risk of impact or trauma on the vessel walls. It is theorized that the reduction in the risk of thrombosis may be at least partly due to the more intermittent and random nature of the interaction of these portions of the body of the device with the vessel walls which reduces the indwelling time required for effective fibrosis of the device against the vessel wall, and also tends to reduce the size of any thrombosis formed on the device. With respect to thrombosis and fibrosis at the distal portion of the device, the present invention takes advantage of the fact that stenosis of the cephalic vein, the innominate vein or the subclavian vein is less critical than stenosis of many other veins and that closure or loss of those veins is not life threatening.

In another embodiment, the anchoring of the intravascular implantable device superior to the heart in accordance with the present invention, such as in the pectoral region, for example, provides for easier bailout in the event of a problem with the device requiring explantation or in the event that the device is to be removed and replaced with, for example, a conventional can-based device.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 4 is a cross-sectional plan view of an implantable intravascular pacing device according to another embodiment of the present invention.

FIG. 5 is a cross-sectional plan view of an implantable intravascular pacing device according to another embodiment of the present invention.

FIG. 7 is a perspective view an implantable intravascular defibrillation device according to one embodiment of the present invention.

FIG. 8 is a perspective view of an anchoring arrangement according to a further embodiment of the present invention.

FIG. 9 is an exploded view of the anchoring arrangement of FIG. 8.

FIG. 10 is a perspective view of an anchor and cleat according to one embodiment of the present invention.

FIG. 10A is a closeup detail view of FIG. 10, depicting the connection between the cleat and the anchor.

FIG. 10B is a side plan view of FIG. 10.

FIG. 10C is a top plan view of FIG. 10.

Figure 1:
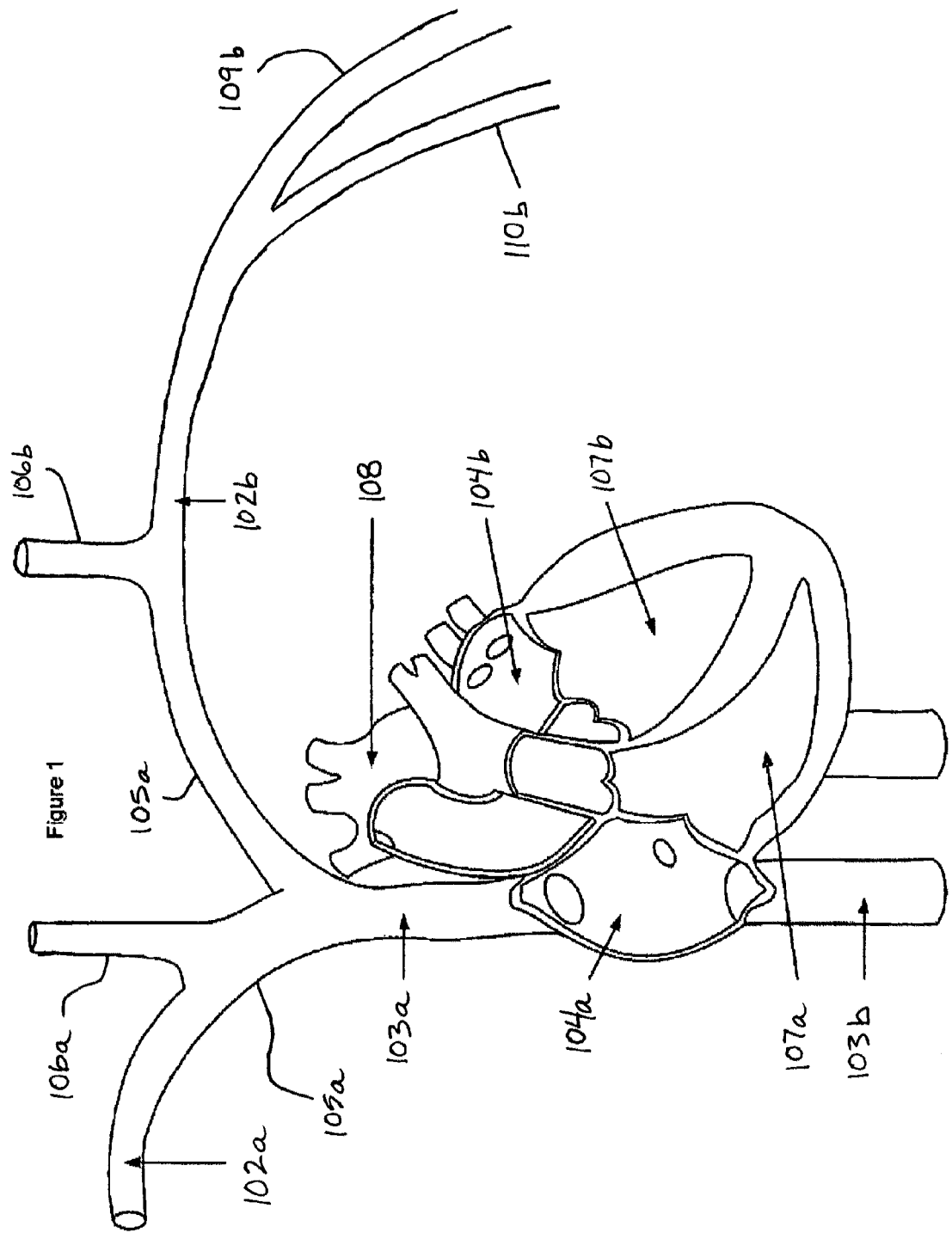
FIG. 1 is a perspective illustration depicting human cardiac anatomy.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the claims.

DETAILED DESCRIPTION OF THE EMBODIMENTS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Referring now to FIG. 1, the general cardiac anatomy of a human is depicted, including the heart and major vessels. The following anatomic locations are shown and identified by the listed reference numerals: Right Subclavian 102a, Left Subclavian 102b, Superior Vena Cava (SVC) 103a, Inferior Vena Cava (IVC) 103b, Right Atrium (RA) 104a, Left Atrium (LA) 104b, Right Innominate/Brachiocephalic Vein 105a, Left Innominate/Brachiocephalic Vein 105b, Right Internal Jugular Vein 106a, Left Internal Jugular Vein 106b, Right Ventricle (RV) 107a, Left Ventricle (LV) 107b, Aortic Arch 108, Descending Aorta 109, Right Cephalic Vein 109a (not shown in FIG. 1), Left Cephalic Vein 109b, Right Axillary Vein 110a (not shown in FIG. 1) and Left Axillary Vein 110b.

One embodiment of the present invention describes intravascular electrophysiological systems that may be used for a variety of functions to treat cardiac arrhythmias with electrical stimulation. These functions include defibrillation, pacing, and/or cardioversion. In general, the elements of an intravascular implantable device for electrophysiological therapy include at least one device body and typically, but optionally, at least one lead coupled to the body. While the present invention is directed to anchoring and retention of the device body of an intravascular implantable device, it will be understood that, in some embodiments, the one or more leads may also be anchored or retained in the vasculature or within the heart. Alternatively, the intravascular implantable device may have no leads, such as for an embodiment of an intravascular implantable drug/gene therapy device, or the one or more leads may not be anchored or retained in the vasculature or within the heart.

Various examples of intravascular implantable electrophysiology devices, such as intravascular defibrillation and/or pacing devices 20 and leads 28 will be given in this description. In those examples, reference numerals such as 20a, 20b, 20c, etc., will be used to describe certain embodiments of the intravascular device 20, whereas elsewhere reference numeral 20 may be used to more generally refer to intravascular devices of the type that may be used with the present invention for providing therapy other than, or in addition to, cardiac electrophysiology. Likewise, reference number 28 may be used generally to refer to leads of a type that may be used with the system. Reference number 100 refers generally to vessels and/or vessel walls within the human body.

In one embodiment, device 20 includes components, known in the art to be necessary to carry out the system functions of an implantable electrophysiology device. For example, device 20 may include one or more pulse generators, including associated batteries, capacitors, microprocessors, communication circuitry and circuitry for generating electrophysiological pulses for defibrillation, cardioversion and/or pacing. Device 20 may also include detection circuitry for detecting arrhythmias or other abnormal activity of the heart. The specific components to be provided in device 20 will depend upon the application for the device, and specifically whether device 20 is intended to perform defibrillation, cardioversion, and/or pacing along with sensing functions.

Device 20 can be proportioned to be passed into the vasculature and to be anchored within the vasculature of the patient with minimal obstruction to blood flow. Suitable sites for introduction of device 20 into the body can include, but are not limited to, the venous system using access through the right or left femoral vein or the right or left subclavian vein. For purposes of describing the present invention, the various portions of the device 20 will be referenced to the location of those portions, the proximal portion 22, the distal portion 24 and the middle portion 26 relative to the introduction site in the femoral vein. Device 20 generally includes a proximal end and a distal end. It will be understood, however, that if an alternate access site were used to introduce the device 20, such as the subclavian veins, the various portions 22, 24 and 26 of the device 20 would be referenced relative to the inferior/superior location of the device 20 within the vascular system in the torso of a patient. In one embodiment, distal portion 24 may be defined as being part of the device body, encompassing up to the distal-most third of the body of device 20. In another embodiment, distal portion 24 may be defined as encompassing part of the body of device 20 and part of tether portion 52. In a further embodiment, distal portion 24 is defined as not encompassing the device body at all, rather it encompasses tether portion 52.

In one embodiment, the device 20 can have a streamlined maximum cross sectional diameter which can be in the range of 3-15 mm or less, with a maximum cross-sectional diameter of 3-8 mm or less in one embodiment. The cross-sectional area of device 20 in the transverse direction (i.e. transecting the longitudinal axis) can preferably be as small as possible while still accommodating the required components. This area can be in the range of approximately 79 mm2 or less, in the range of approximately 40 mm2 or less, or between 12.5-40 mm2, depending upon the embodiment and/or application.

In one embodiment, the cross-section of device 20 (i.e., transecting the longitudinal axis) may have a circular cross-section, although other cross-sections including crescent, flattened, or elliptical cross-sections may also be used. It can be highly desirable to provide the device with a smooth continuous contour so as to avoid voids or recesses that could encourage thrombus formation on the device. It can also be desirable to provide for a circular cross-section to aid in removal or explantation of the device that more easily permits the device to be torqued or rotated during the removal or explantation to break free of any thrombosis or clotting that may have occurred. In one embodiment, the cross-section of device 20 is generally isodiametric along the entirety of its longitudinal length other than for tapered portions at the proximal and distal ends of the device 20. In one embodiment, the aspect ratio of the cross-section of the device 20 to a longitudinal length of the body portion of the device 20 is less than 1:10 (e.g., 10 mm diameter to 10 cm length) and in another embodiment is less than 1:50.

In one embodiment, the housing of device 20 may be covered by an electrically insulative layer or coating such as ePTFE. It may be desirable to provide a coating that is anti-thrombogenic (e.g., perfluorocarbon coatings applied using supercritical carbon dioxide) so as to prevent thrombus formation on device 20. It may also be beneficial that the coating have anti-proliferative properties so as to minimize endothelialization or cellular in growth, since minimizing growth into or onto device 20 will help minimize vascular trauma when the device is explanted. The coating may thus also be one which elutes anti-thrombogenic compositions (e.g., heparin sulfate) and/or compositions that inhibit cellular in growth and/or immunosuppressive agents. If the housing of device 20 is conductive, this layer or coating may be selectively applied or removed to leave an exposed electrode region on the surface of the housing where necessary, such as depicted in FIGS. 2-6A.

In some embodiments one or more leads 28 may extend from device 20 proximate any of the various portions 22, 24 and 26 of the device 20. In the embodiment shown in FIGS. 2, 3, and 6, for example, a single lead 28 is shown, extending from the proximal end 22 of device 20. A lead 28 includes one or more electrodes, such as tip electrodes, ring electrodes, or defibrillation electrodes. In embodiments having a tether portion 52, a lead 28 may be included within tether portion 52. If two leads 28 are used, they may extend from opposite ends of device 20, or they may extend from the same end of the device 20, such as depicted in FIGS. 4-5. Either or both of the leads may be equipped to sense electrical activity of the heart. Monitoring of the heart's electrical activity is needed to detect the onset of an arrhythmia. Activity sensed by the sensing electrode(s) is used by device 20 electronics to trigger delivery of a defibrillation shock that in one embodiment may be delivered via lead 28 having a defibrillation electrode or delivery of a pacing impulse that in one embodiment may be delivered via lead 28 via a pacing electrode.

The lead 28 may be a conventional defibrillation/pacing lead, although alternative lead configurations may be desirable if warranted by the desired placement of the device 20 and lead within the body. An optimal lead will preferably give the physician implanting the device flexibility to position the device at an appropriate location in the chosen vessel without concern that the leads extending from the device will not reach their intended location. Thus, for some patients it may be necessary to use a lead that is slightly longer than conventional leads, or the lead may include a coiled section that is similar to the configuration of a coiled telephone cord. A coiled section can allow elongation of the effective length of the lead when tension is applied to the coil. The coiled section or any alternate type of yieldable lead section may be a plastically deformable metal or polymer that will retain its extended configuration after it has been stretched to that configuration. Other configurations that will allow additional lead length to pull out from the device if needed may also be used.

Figure 11:
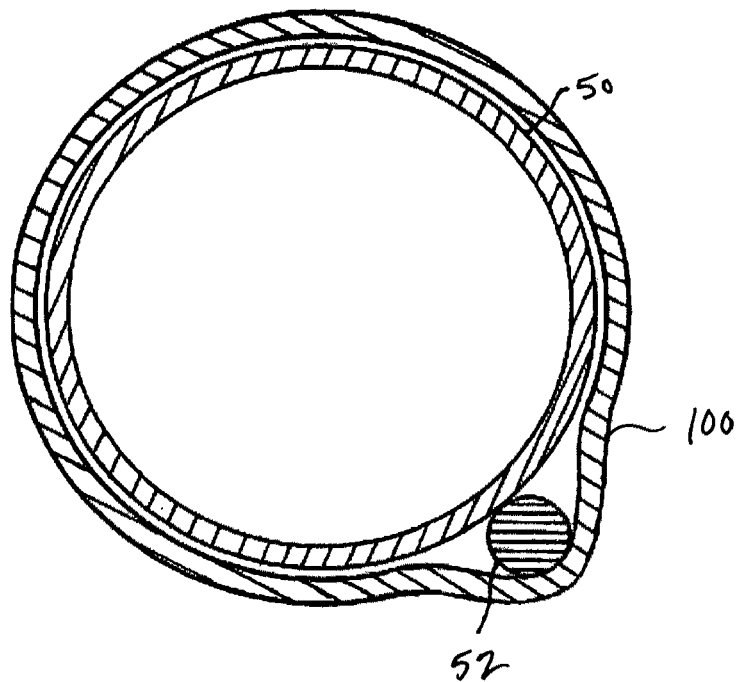
FIG. 11 is a cutaway view of one embodiment of an anchor arrangement implanted within a vessel.

For leads 28 that are to be positioned within a chamber of the heart such as in FIG. 11, the lead may include a helical screw-in tip or be of the tined variety for fixation to the cardiac tissue. A detachable screw-in lead tip may be provided, which allows the lead tip to be left within the chamber of the heart when lead 28 is extracted.

Lead 28 may have a steroid-eluding tip to facilitate tissue in-growth for fixation purposes, or may include non-thrombogenic and/or non-proliferative surfaces or coatings similar to those as may be applied to device 20. For example, lead 28 may include a coating that is anti-thrombogenic (e.g. perfluorocarbon coatings applied using supercritical carbon dioxide) so as to prevent thrombus formation on the lead. It is also beneficial for the coating to have anti-proliferative properties so as to minimize endothelialization or cellular ingrowth, since minimizing growth into or onto the lead will help minimize vascular trauma when the device is explanted. The coating may thus also be one which elutes anti-thrombogenic compositions (e.g. heparin sulfate) and/or compositions that inhibit cellular in-growth and/or immunosuppressive agents.

It should be appreciated that in this disclosure the term "lead" is used to mean an element that includes conductors and electrodes in an elongated, sealed and insulated protective configuration that is adapted to withstand chronic implantation and is generally floppy in flexibility to permit the electrodes to be positioned somewhat remotely from the circuitry that energizes the electrodes via the conductors. The lead 28 may be integrated with the device body, or attachable to the device body in situ or prior to implantation, or the lead 28 may be integral with the device body as an extension of the device itself. Thus, leads may include elements that are simply extensions or tapers of the device 12a itself (such as the portion of the device 12a at which electrodes 22a are located) as well as more conventional leads. More than one lead 28 may be provided, and leads may be included on the proximal/inferior end of the device body, on the distal/superior portion of the device body, generally on the device body, and/or any combination thereof. In one embodiment, an end of the device body may be modified to include a stepped portion proximate the lead connection, such as on the proximal end of the device. The stepped portion allows a smooth transition between the exterior surface of the lead and the device body.

Figure 2:
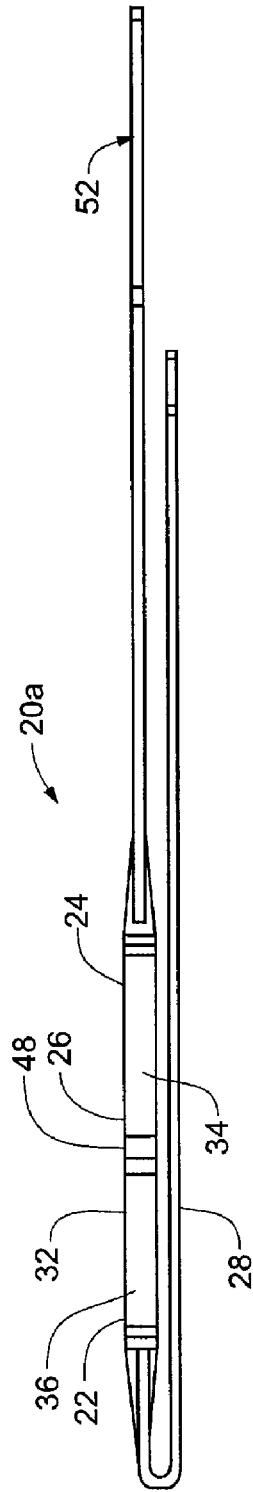
FIG. 2 is a cross-sectional plan view of an implantable intravascular pacing device according to one embodiment of the present invention.
Figure 2A:
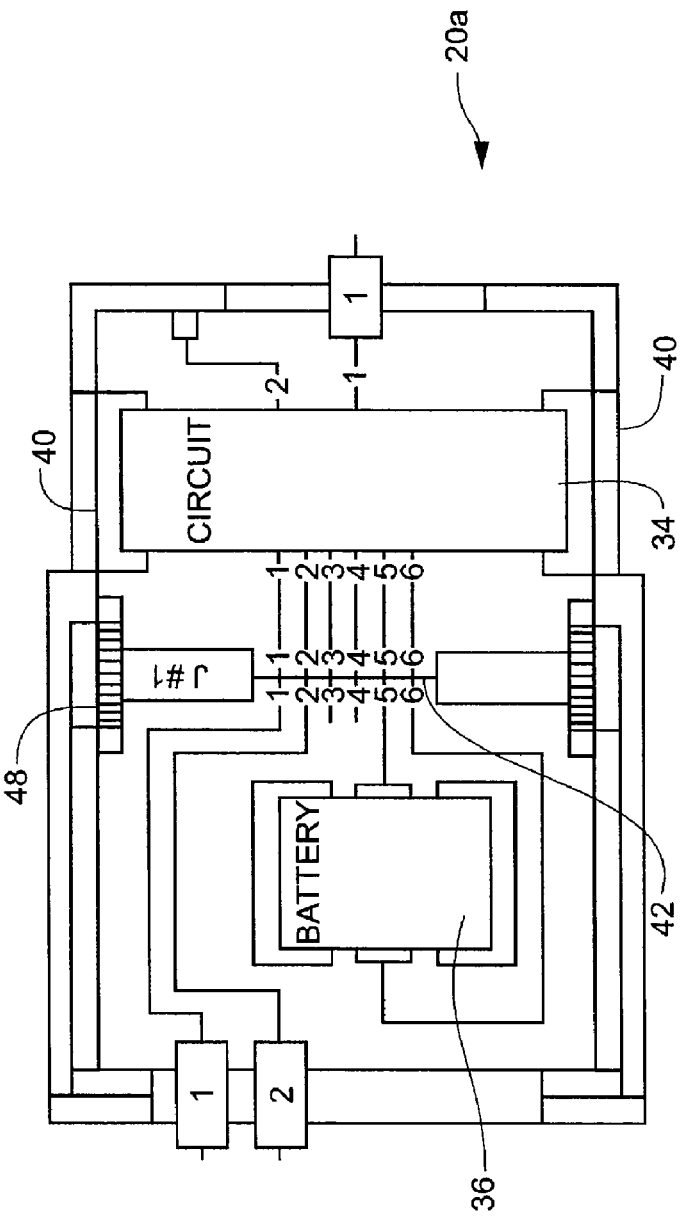
FIG. 2A is a schematic representation of FIG. 2.

Given the minimal space allowed for components, it is desirable to arrange the components within device 20 so as to make efficient use of the available space. Examples of devices having space efficient arrangements of their contents are shown in FIGS. 2-6A. One example is identified by reference numeral 20a in FIG. 2. One embodiment of device 20a includes one or more elongate housings or enclosures 32 depicted in cross-section in FIG. 2A to allow the components housed within it to be seen. In one embodiment, enclosure 32 is a rigid or semi-rigid housing preferably formed of a material that is conductive, biocompatible, capable of sterilization and capable of hermetically sealing the components contained within the enclosure 32. One example of such a material is titanium, although other materials may also be used.

Within enclosure 32 are the electronic components 34 that govern operation of the device 20a. For example, components 34a are associated with delivery of a defibrillation pulse via a lead 28 (FIG. 6), whereas components 34b are associated with the sensing function performed using sensing electrodes on the defibrillation lead, on a separate lead 28 (e.g., FIGS. 4 and 5), or on the device body itself. Isolating components 34a from components 34b may be desirable if noise generated by the high voltage defibrillation circuitry 34a during charging might interfere with performance of the sensing circuitry 34b, or if practical limitations exist with respect to circuit interconnects 42.

Device 20a further includes one or more batteries 36 for supplying power to the device, and in some embodiments, and/or one or more exposed body electrodes 40 on an exterior surface of enclosure 32. One or more circuit interconnects 42 can provide the electrical coupling between the electronic components 34, one or more leads 28, electrode(s) 40, and batteries 36. Additional circuitry may be provided to facilitate recharging batteries 36.

Figure 3:
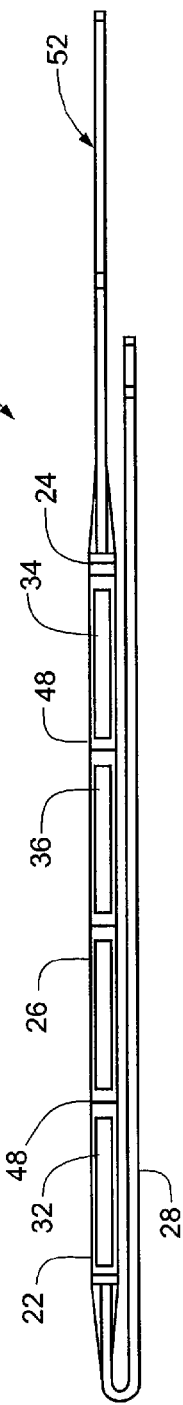
FIG. 3 is a cross-sectional plan view of an implantable intravascular pacing device according to another embodiment of the present invention.
Figure 3A:
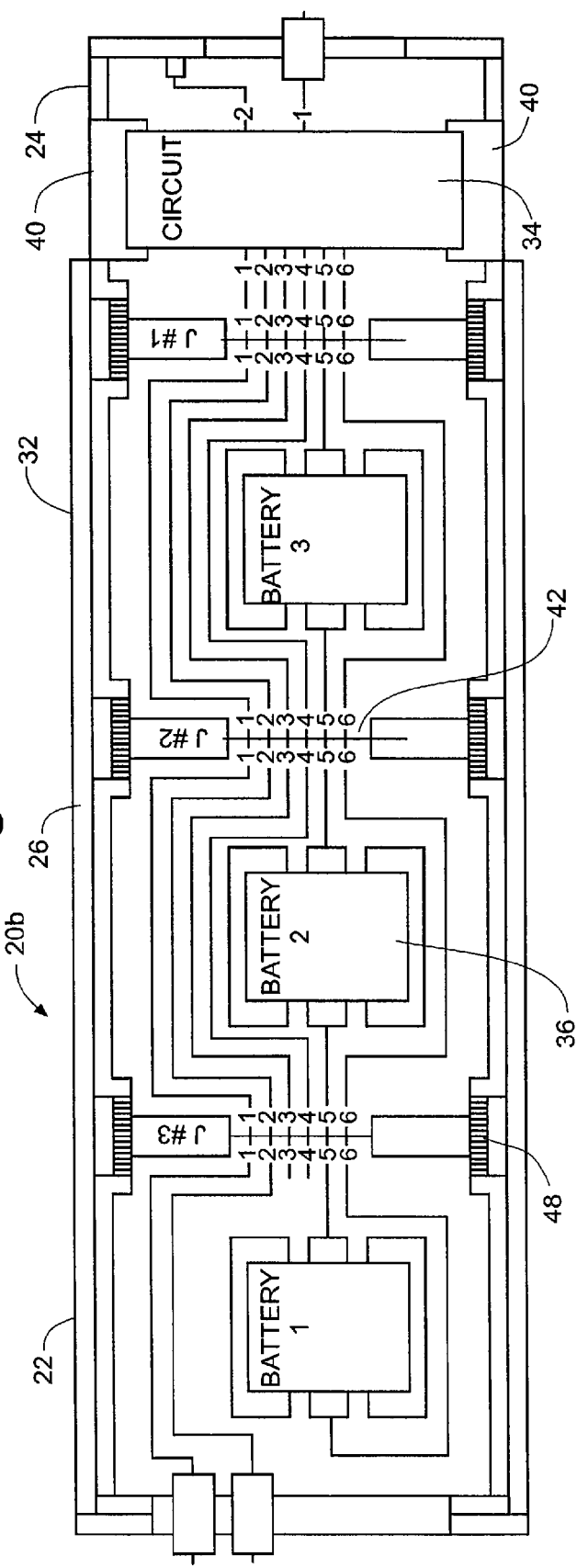
FIG. 3A is a schematic representation of FIG. 3.

A second example of an arrangement of components for the intravascular implantable pacing device is identified by reference numeral 20b and shown in FIGS. 3-3A. As depicted in FIGS. 3-3A, the components of device 20b may be arranged in series with one another to give device 20b a streamlined profile. Because device 20b is intended for implantation within the patient's vasculature, some flexibility is desired so as to allow the elongate device to be easily passed through the vasculature. Flexibility may be added by segmenting device 20b, such as by forming one or more breaks in the enclosure, and by forming one or more hinge zones or bellows at each break which form dynamic flexible zones that can bend relative to the longitudinal axis of the device 20b in response to passage and/or positioning of device 20b though curved regions of the vasculature.

In device 20b, each segment may be separately enclosed by its own titanium (or similar) enclosure in the form of containers or compartments 32. The components within the containers 32 may be electrically connected by flexible circuit connects 42, for example. In one embodiment, the containers 32 are connected using a flexible material such as silicone rubber filler to form hinge zones. In another embodiment, flexible device 20 includes one or more rigid enclosures or containers 32 used to contain electronic components 34 to be implanted inside the vasculature of a patient and having the hinge zones formed of a bellows arrangement 48.

Containers 32 can be of any appropriate shape, cross-section, and length, but in this example are shown to have a cylindrical shape with a diameter of approximately 3-15 mm and a length of approximately 20 mm to 75 mm. Containers 32 can be used to house electromechanical parts or assemblies to form sophisticated implantable devices such as defibrillators, pacemakers, and drug delivery systems. Any appropriate number of these containers 32 can be combined using interconnecting bellows 48. Interconnecting mechanical bellows 48 can be used, to connect a number of rigid containers 32 in order to form a flexible device 20. For many devices, this will include a string of at least three containers 32. In one embodiment, the aspect ratio of the cross-sectional diameter to the longitudinal length of each container is less than at least 1.5:2 (e.g., 15 mm diameter to 20 mm length) and in another embodiment the aspect ratio is at least 1:4.

In one embodiment, the bellows 48 can be of any appropriate shape, but can preferably have a shape similar in cross-section to the cross-section of the container, in order to prevent the occurrence of edges or ridges that can give rise to problems such as the formation of blood clots in the vasculature. The bellows can be made of a biocompatible material similar to the containers. Any coatings used for electrically insulating the containers and/or making the containers more hemo-dynamically compatible also can be used with the bellows.

In addition to the ability of the bellows 48 to bend away from the central or long axis of device 20, the bellows 48 also allow for flexibility along the central axis of the device. The ability to flex along the central axis provides shock absorption in the long axis as well as 3-dimensional flexing. Shock absorption can help to protect device 20 and internal components during the implant process by minimizing the motion of the implanted device. Further, shock absorption can provide a 1:1 torque ratio for steering during the implant process. The shock absorption also can help during the life of device 20, as the natural movement of the body of a patient can induce some stress on the device 20.

For a more detailed explanation of the various embodiments of the bellows arrangements 48, reference is made to U.S. Published Patent Application Nos. 2006/0217779, filed Mar. 24, 2005, and 2007/0265673, filed Apr. 3, 2007, the disclosures of each of which are hereby incorporated by reference herein.

Figure 5A:
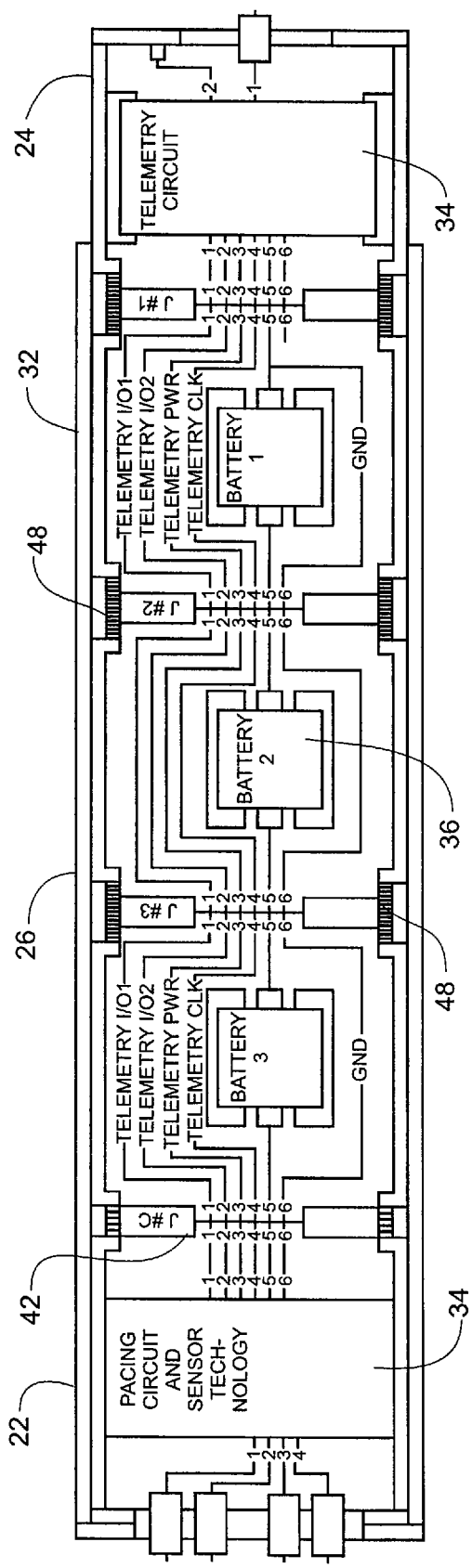
FIG. 5A is a schematic representation of FIG. 5.

Referring now to FIGS. 4-5A, another embodiment of the device, identified by reference numeral 20c, is depicted. Device 20c is similar to the embodiment depicted in FIGS. 3-3A, however device 20c includes multiple leads 28 on the proximal portion 22 of device 20c.

Figure 6:
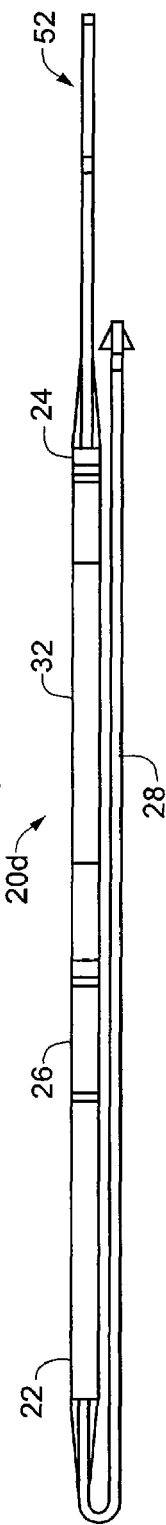
FIG. 6 is a cross-sectional plan view of an implantable intravascular defibrillation device according to one embodiment of the present invention.
Figure 6A:
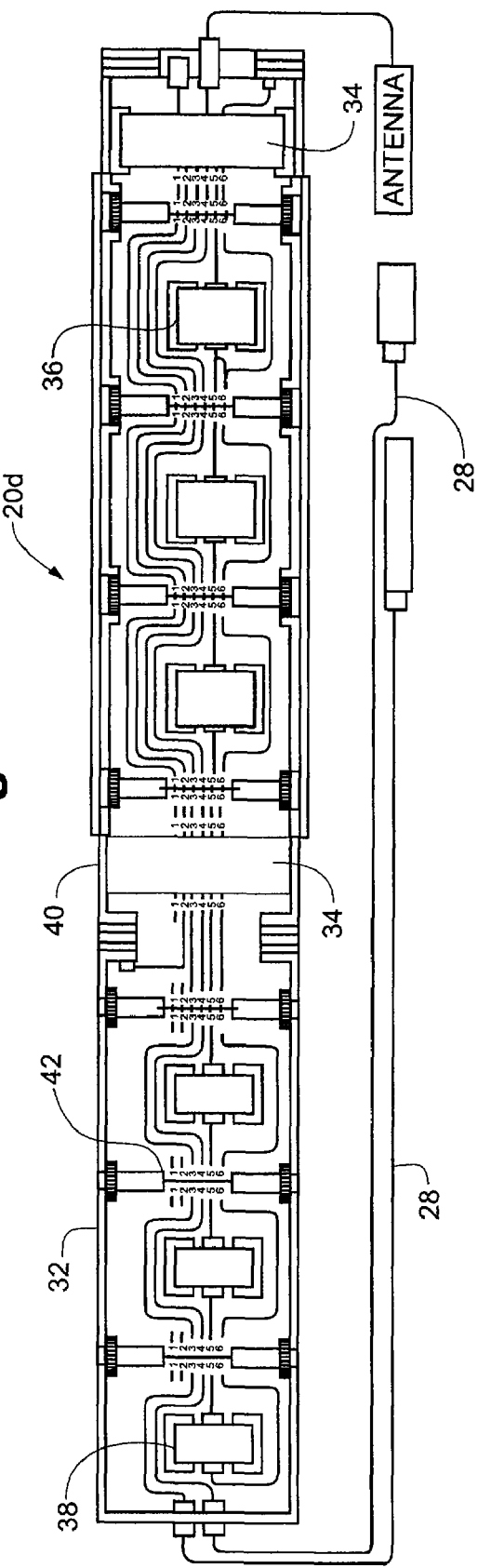
FIG. 6A is a schematic representation of FIG. 6.

Referring now to FIGS. 6-6A, another embodiment of the device identified by reference numeral 20d is depicted. Device 20d is an intravascular implantable defibrillation device, having a lead 28 adapted to inserted into the right ventricle of a patient. Device 20d further includes one or more sensing electrodes, which may be located on the exterior of enclosure 32, similar to body electrodes 40. Device 20d also includes one or more defibrillation electrodes on the exterior of enclosure 32.

Referring again generally to device 20, the device is preferably able to communicate via wireless telemetry to an instrument outside of the patient's body. This is commonly referred to as device interrogation and/or programming and allows the physician to monitor the state and performance of the device. It also allows the physician to reconfigure the device in the case of programmable settings. The circuitry used for device interrogation and/or programming can be included in all of device 20 embodiments, with the device telemetry antenna either encapsulated within the device enclosure or as part of the tether potion 52 discussed in more detail below. The circuitry may include a circuit that will respond in the presence of a magnetic field, electric field, a near-field or a far-field, all which are features also known in the implantable device industry.

These communication techniques, either alone or in various combinations, are intended to allow device 20 to communicate the device's status to the physician. For example, the status information may include the state of the battery system, and whether or not a therapeutic energy delivery had occurred or not. The communication might also identify the parameters device 20 used, including stored electrograms, to allow reconstruction of the delivery episode by the instrument. The telemetry feature may also be used to program certain features governing function of device 20, such as the threshold heart rate in beats per minute which, when detected by the device, will cause the device to provide appropriate energy therapy.

Referring now to FIGS. 7-16, in one embodiment distal portion 24 of device 20 includes a tether portion 52. During implantation according to one embodiment, device 20 is routed through the inferior vena cava 103b, through superior vena cava 103a, and then on to one of a number of locations superior to the superior vena cava 103a as will be described. Device 20 is then anchored within the vasculature using an anchor 50.

Anchor 50 is configured to retain device 20 within a patient's vasculature, and in one embodiment anchor 50 comprises a conventional intravascular stent. In one embodiment, the anchor 50 may include features that give some structural stability to cause the anchor to radially support device 20 against a vessel wall 100. For example, a mesh or other framework formed of shape memory (e.g., nickel titanium alloy, nitinol or shape memory polymer) elements or stainless steel wires may be used to form anchor 50. In another embodiment, the anchor 50 is provided with a smooth polymeric barrier that is both anti-proliferative and anti-thrombogenic and that thereby prevents endothelial growth and thrombus formation on the anchor. Examples of materials for the polymeric barrier include, but are not limited to ePTFE, or other fluoropolymers, silicone, non-woven nylon, or biomimetic materials. The polymeric barrier is preferably formed by layers of barrier material on the interior and exterior surfaces of the framework, although it will be appreciated that the framework and barrier may be combined in a variety of ways to prevent thrombus formation and endothelialization on the anchor walls. As one alternative (or in addition to the polymeric barrier), the anchor material could include surfaces for eluting non-coagulative, anti-platelet (e.g. IIBIIIA glycoprotein receptor blockers), anti-proliferative, and/or anti-inflammatory substances. Additional information pertaining to the construction, materials and operation of anchors suitable for use with the present invention are described in U.S. Pat. No. 7,082,336 and U.S. Published Patent Application No. 2004/0249431, the disclosures of each of which are hereby incorporated by reference herein.

In one anchoring embodiment, the anchor relies solely on a non-biological fixation to secure the anchor within the vessel, such as mechanical fixation by the radial expansion force of an anchor 50 or hooking, latching, catching or cleating the anchor 50 with respect to the vessel. In another embodiment, the mechanical fixation may be augmented with by a glue or other non-biological adhesive interfaced between the anchor and the vessel which for purposes of the present invention would be considered part of a non-biological, as opposed to biological, fixation of the anchor. In still another embodiment, the fixation of the anchor may be accomplished solely by a glue or other non-biological adhesive interfaced between the anchor and vessel. In another embodiment, the anchor may eventually rely on biological fixation such as from endothelialization or thrombus formation to assist in retaining the anchor within the vessel in addition to the initial non-biological fixation at the time of implantation.

Figure 12:
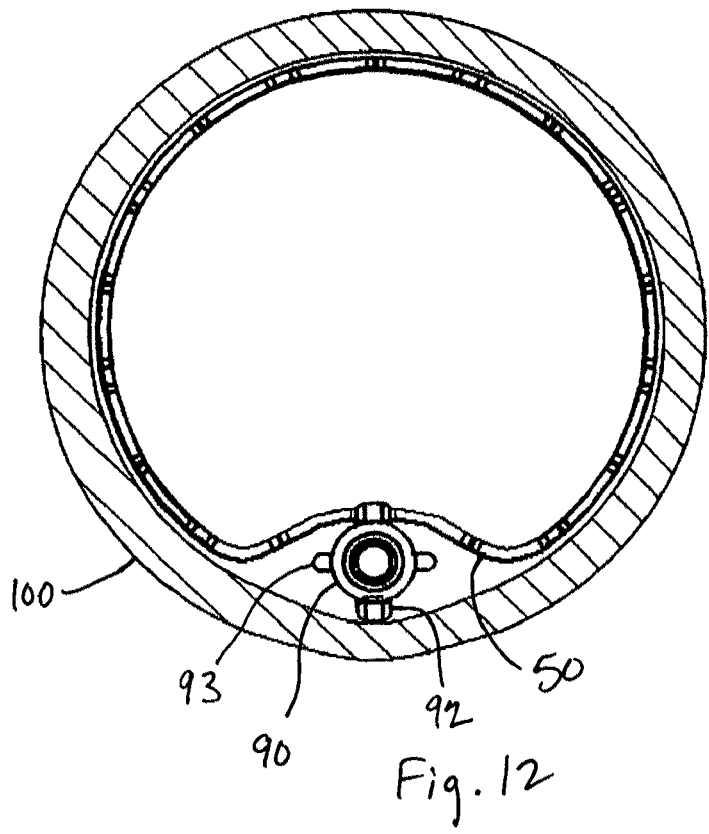
FIG. 12 is a cutaway view of a further embodiment of an anchor arrangement implanted within a vessel.

Referring now to mechanical fixation anchoring embodiments, device 20 may generally be anchored by active or passive means. In one passive anchoring embodiment, tether portion 52 may be secured by being "sandwiched" between a vessel wall 100 and anchor 50, as depicted in FIG. 11. In one active anchoring embodiment, tether portion 52 may be secured by a mechanical coupling with anchor 50, such as depicted in FIGS. 8 and 12.

Anchor 50 may be separate from tether portion 52, although in one embodiment anchor 50 may also be integrated with tether portion 52. In an alternate embodiment, anchor 50, either integrated or separable, may be used to secure the body of the device 20 at the distal portion 24, where the body does not include a unique tether portion 52. In one embodiment, the tether portion 52 is selectively detachable from the body of the device 20 to facilitate extraction and/or explantation of the device 20. Device 20 is preferably able to communicate via wireless telemetry to an instrument outside of the patient's body and in one embodiment, tether portion 52 may include an internal antenna to facilitate device interrogation and/or programming. In another embodiment, the internal antenna is not within detachable portion 52. For more details of the various embodiments of the tether portion 52, reference is made to Provisional Application No. 60/868,434, filed Dec. 4, 2006, the disclosure of which has been incorporated by reference herein.

In one embodiment, tether portion 52 is preferably of a smaller diameter than device 20. Minimizing the diameter of tether portion 52 is desirable so as to reduce bulging and/or irritation of the vessel 100. In one embodiment, tether portion 52 is sufficiently flexible to allow bending during implantation, yet is more rigid than the floppy flexibility of leads 28. In one embodiment, tether portion 52 includes a retention tip 60, which is configured to prevent tether portion 52 from being pulled out from anchor 50. Tip 60 functions as a stop, interfering with the distal end of anchor 50 and preventing tether 52 from being pulled out from between anchor 50 and vessel wall 100.

In another embodiment, tether portion 52 may include an electrode for defibrillation, pacing, or sensing of cardiac electrical activity. The use of an electrode positioned in tether portion 52 may be especially useful for defibrillation to generate a shock vector across the heart.

Referring now to FIGS. 8-10C and 12, one embodiment of a tether portion 52 is depicted. Tether 52 is coupleable to a device 20, and may include a passage suitable for insertion of a guidewire to assist in implantation. As with other embodiment, tether 52 may also include an antenna for communication purposes. Referring to FIG. 9, a cleat 90 is depicted, being configured to couple to tether 52 and an anchor 50. Cleat 90 includes one or more features for coupling to anchor 50, such as clips 92 which are configured to interact with the mesh features of anchor 50. One or more fins 93 are disposed on the cleat body. A platform area 94 may be provided on cleat 90, the platform providing a suitable surface for deploying a self-expanding anchor therefrom during implantation. Cleat 96 also may include a connection point for coupling to tether 52, and includes one or more attachment features 96. Cleat 90 may be configured to be removably coupled to tether 52, or integrated therewith, or may be molded to tether 52, or other connection arrangements as will be appreciated by one skilled in the art.

The design of cleat 90 is configured to correctly orient the cleat during implantation such that engagement of anchor 50 is easy to achieve. The placement of clips 92 and fins 93 act together, such that when cleat 90 is in a target vessel, any rotational orientation of the cleat will result in one of clips 92 being able to be engaged with anchor 50. In an embodiment wherein anchor 50 comprises a stent, cleat 90 may be adapted to couple to a strut 51 of stent 50.

Referring now to the implantation of device 20, specific details of various implantation embodiments are discussed in U.S. Provisional Application titled "Implantation Methods, Systems and Tools for Intravascular Implantable Devices", filed Dec. 3, 2007, the disclosure of which has been incorporated by reference herein.

In one general embodiment, device 20 is implanted by making an incision in the patient's femoral vein, and inserting an introducer sheath through the incision into the vein. The introducer sheath keeps the incision open during the procedure, and includes a seal adapted to prevent blood from exiting the body while allowing the insertion of various tools and devices into the body. Device 20 may be introduced in a number of ways. In one embodiment, the device 20 may be introduced by an over-the-wire technique. The distal end or distal portion of device 20 is provided with a passageway configured to receive a guidewire, and the device is slid onto the guide wire, then the distal end of device 20 is introduced through the seal. Device 20 is guided through the vasculature of the patient, into the inferior vena cava, then the superior vena cava, and into the subclavian vein or other vessel superior to the heart. A device delivery catheter may be used to facilitate introducing the device.

Next, the anchor 50 is introduced. Anchor 50 may be inserted through the seal in the femoral incision used to implant device 20. In another embodiment, anchor 50 is inserted from another incision such as through an incision closer to the location of tether portion 52. In one embodiment, anchor 50 may be introduced after device 20 has been positioned at the desired location within the vessel. In another embodiment, anchor 50 may be introduced prior to device 20 being introduced.

Referring to an embodiment wherein anchor 50 is introduced via the femoral incision, the anchor may be delivered over the guide wire, such as with an anchor delivery catheter. Anchor 50, compressed to a streamlined position, is passed through the vasculature and approaches the distal portion of the device where the anchor will interfere with where the wire enters the tip of the device. The guide wire must be removed from the device and guided around the tip of the device to provide a path for the anchor. The anchor is then guided around the device and past the distal-most portion of the device tip. Anchor 50 may be self-expanding and/or it may be expanded using an inflation tool such as a balloon passed into the anchor's central lumen and subsequently inflated. When anchor 50 is expanded, its radial forces engage tether portion 52 and secure tether portion 52 against vessel wall 100, as depicted in FIG. 11. Depending on the characteristics of anchor 50, the expansion force of the anchor against tether portion 52 may cause the vessel wall 100 to bulge outwardly. Alternatively, the anchor 50 may deform around the shape of tether portion 52, leaving vessel 100 at its normal shape. In another embodiment, both anchor 50 and vessel 100 deform to accommodate tether portion 52. It is desirable to minimize the diameter of tether portion 52, to minimize deformation of anchor 50 and/or vessel 100.

Referring now to deployment and/or fixation of the anchor 50, in an embodiment utilizing cleat 90, anchor 50 in its compressed state is guided proximate platform 94 of cleat 90. Using the anchor delivery catheter, a sheath holding the anchor compressed is released, allowing the anchor to radially expand into the vessel. Cleat 90, coupled to device 20 via tether 52, is sandwiched between deployed anchor 50 and vessel wall 100. To secure cleat 90 to anchor 50, device 20 is manipulated, such as by its proximal end, so that cleat 90 is pulled into anchor 50. Clip 92 is then secured onto the mesh of anchor 50, such as depicted in FIGS. 8, 10 and 10A. Device 20 is then secured in the vasculature. A cutaway view of cleat 90 secured to anchor 50 in a vessel 100 is depicted in FIG. 12.

The lead is then delivered and implanted according to the desired application of device 20. Additional details pertaining to the lead can be found in U.S. Provisional Application titled "Implantation Methods, Systems and Tools for Intravascular Implantable Devices", filed Dec. 3, 2007, the disclosure of which has been incorporated by reference herein.

Referring now to the location of device 20 within the vasculature in accordance with the present invention, suitable locations for anchoring device 20 are referred to as superior (i.e., generally above the heart in a direction toward the head) for purposes of describing the various embodiments of the present invention in that these locations are superior of the heart and in some embodiments superior of the superior vena cava 103a. Further, a suitable superior anchoring location proximate a distal portion of the device 20 effectively permits the remainder of device 20 to float, rather than lay, within the vasculature. By allowing the middle and proximal portions of device 20 to move relatively freely within the vena cava, for example, blood is able to flow all around the device, and thrombus formation and endothelial growth will be minimized. Therefore, suitable superior locations for anchoring the distal portion of device 20 include the right or left innominate (brachiocephalic) veins 105a or 105b, the right or left subclavian veins 102a or 102b, the right or left cephalic veins 109a or 109b.

In addition, many of these superior anchoring locations such as the right or left innominate (brachiocephalic) veins 105a or 105b, the right or left subclavian veins 102a or 102b, the right or left cephalic veins 109a or 109b, are veins within the torso where alternative venous drain routes will exist in the event of fibrosis and/or stenosis proximate the anchoring location. Suitable superior anchoring locations further tend to provide for easier bailout in the event of a problem with device 20 requiring explantation by virtue of easier surgical accessibility. Furthermore, all of these locations create an effective anchoring location that is generally oriented transverse to the general direction (in a standing human patient) of gravitational force or drop force on the portion of the device 20 that may reside within the vena cava. The generally transverse orientation to the direction of gravitational or drop force afforded by these locations aids in dissipating these forces without dislodging the anchor 50.

While the distal portion of device 20 potentially could be anchored in the left internal jugular vein 106b or the right internal jugular vein 106a, these veins are less medically desirable locations because the veins are located generally outside the torso and in the neck and therefore will have more potential complications in the event of fibrosis and/or stenosis proximate the anchoring location. The right internal jugular vein 106a is also a less desirable anchoring location due to the challenges associated with drop tests. Similar to the problems associated with anchoring the device lower in the torso, anchoring the present invention in the right internal jugular vein 106a may not adequately secure the implantable device during drop tests that simulate the effect of a patient falling or jumping. This may be due in part to the axis of right internal jugular vein 106a being closely aligned with the axis of superior vena cava 103a, resulting in the anchor and most of the mass of device 20 being vertically aligned, as opposed to providing an anchoring location that is oriented generally transverse to the direction of gravitational or drop force, as previously discussed.

Figure 13:
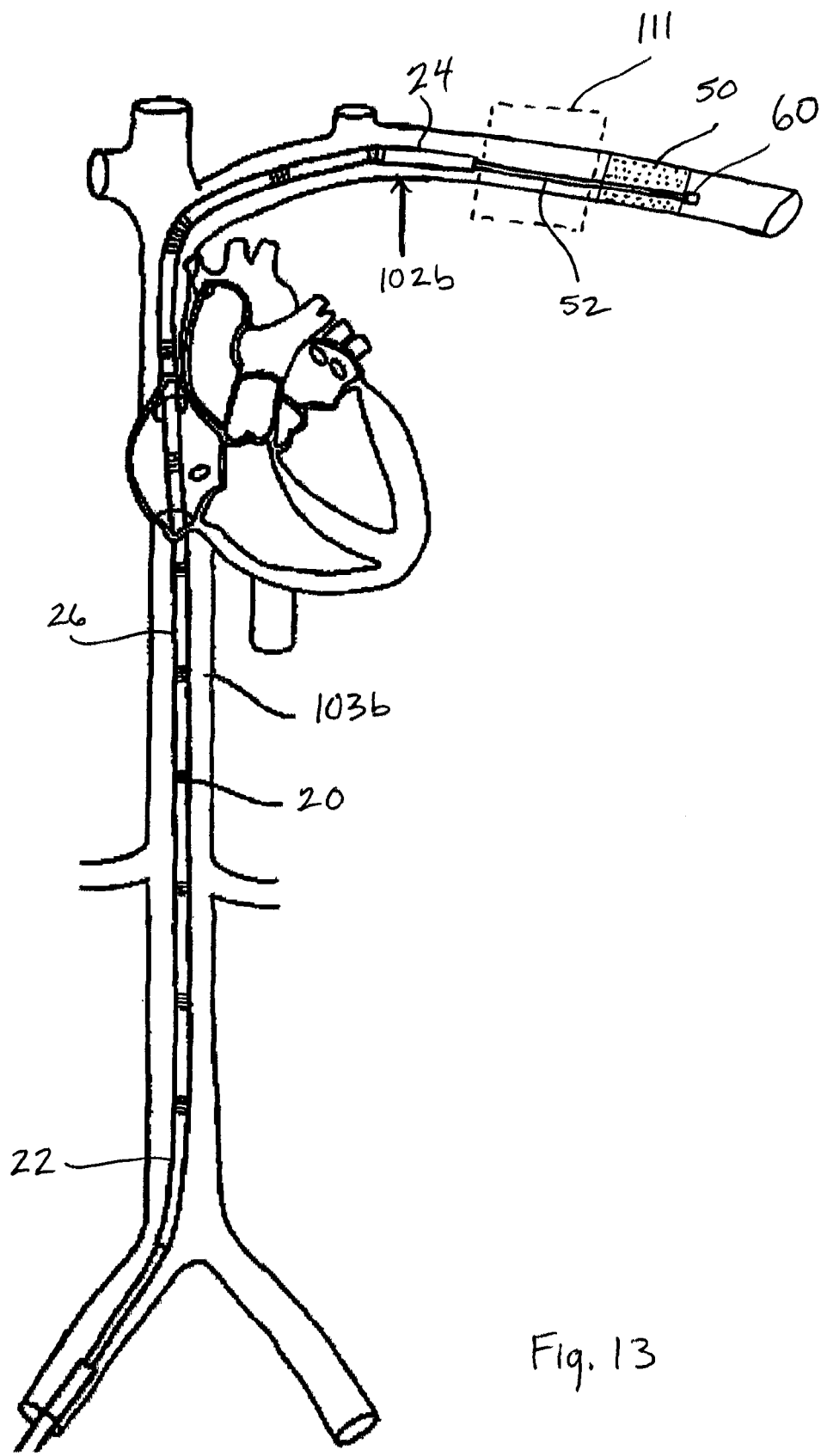
FIG. 13 is a perspective view depicting an anchor arrangement according to the present invention.
Figure 14:
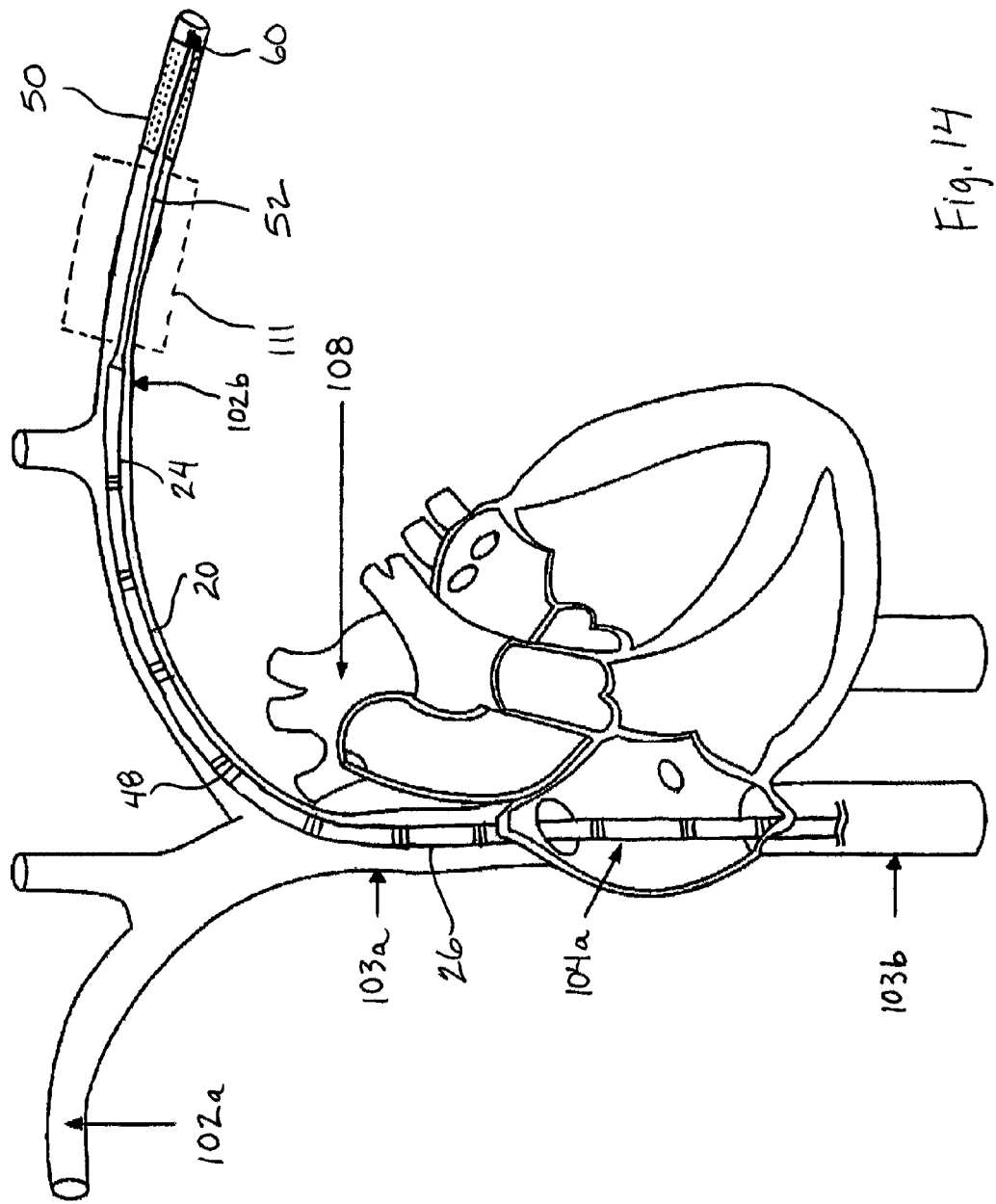
FIG. 14 is a close-up perspective view of FIG. 13.
Figure 15:
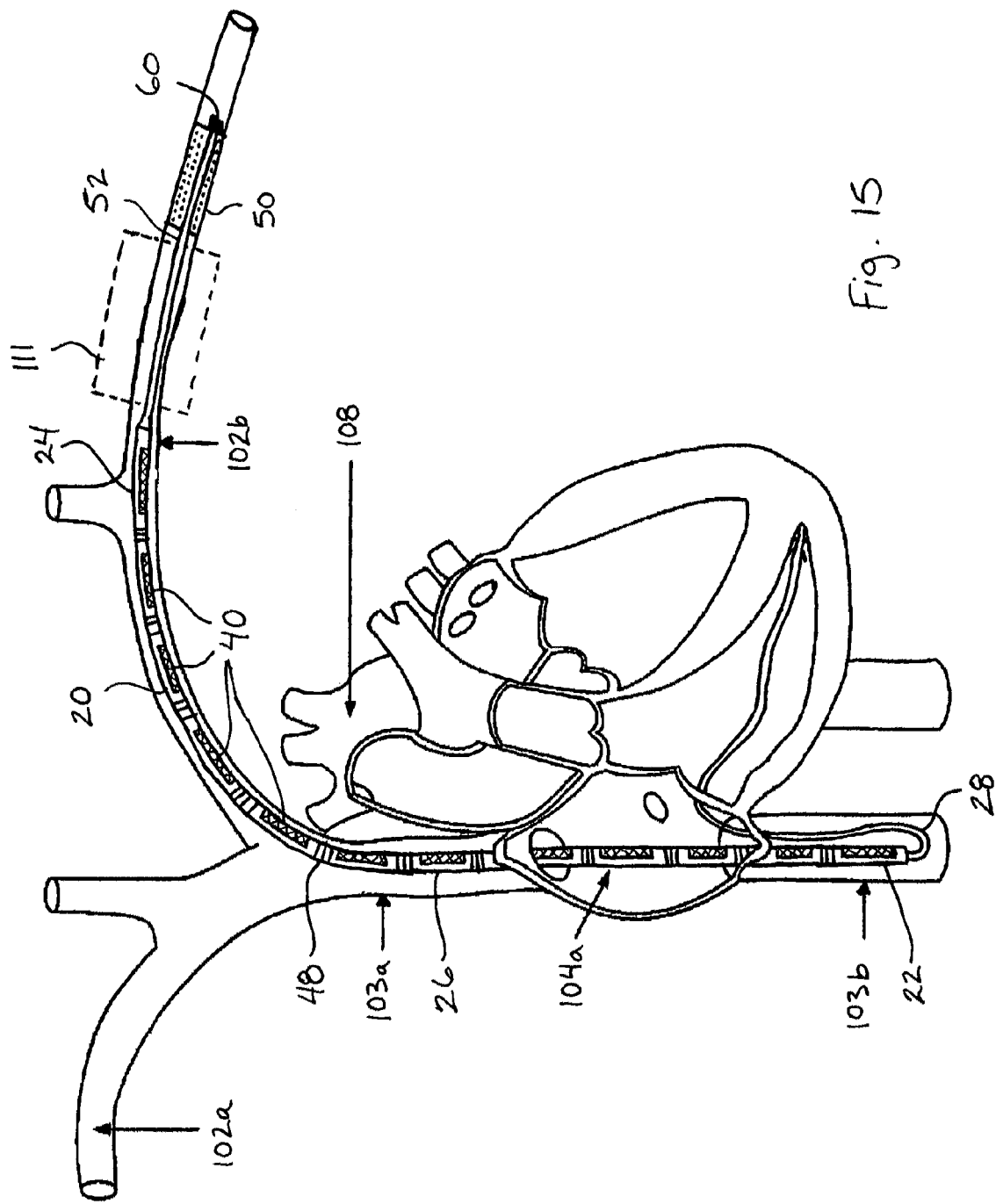
FIG. 15 is a perspective view of one embodiment of the present invention.

A first suitable superior anchor location is proximate the subclavian crush zone 111, which is defined as the region of the right subclavian vein 102a or left subclavian vein 102b that can be compressed between a patient's clavicle and first rib due to upward movement of the patient's arm. Typically, when a foreign object (such as a device body or lead) is introduced intravascularly and placed within subclavian crush zone 111, the object can become damaged, potentially leading to failure of the object or damage to the vessel. This problem is compounded if multiple leads or other intravascular devices are located within the crush zone, as there is a tendency for the leads and/or devices to abrade one another, resulting in an increased potential for failures of the leads and/or devices. In this embodiment, device 20 is positioned proximate subclavian crush zone 111, while tether portion 52 extends across and through the crush zone, and is secured with an anchor 50 located beyond and peripheral of subclavian crush zone 111, as depicted in FIGS. 13-15.

Figure 16:
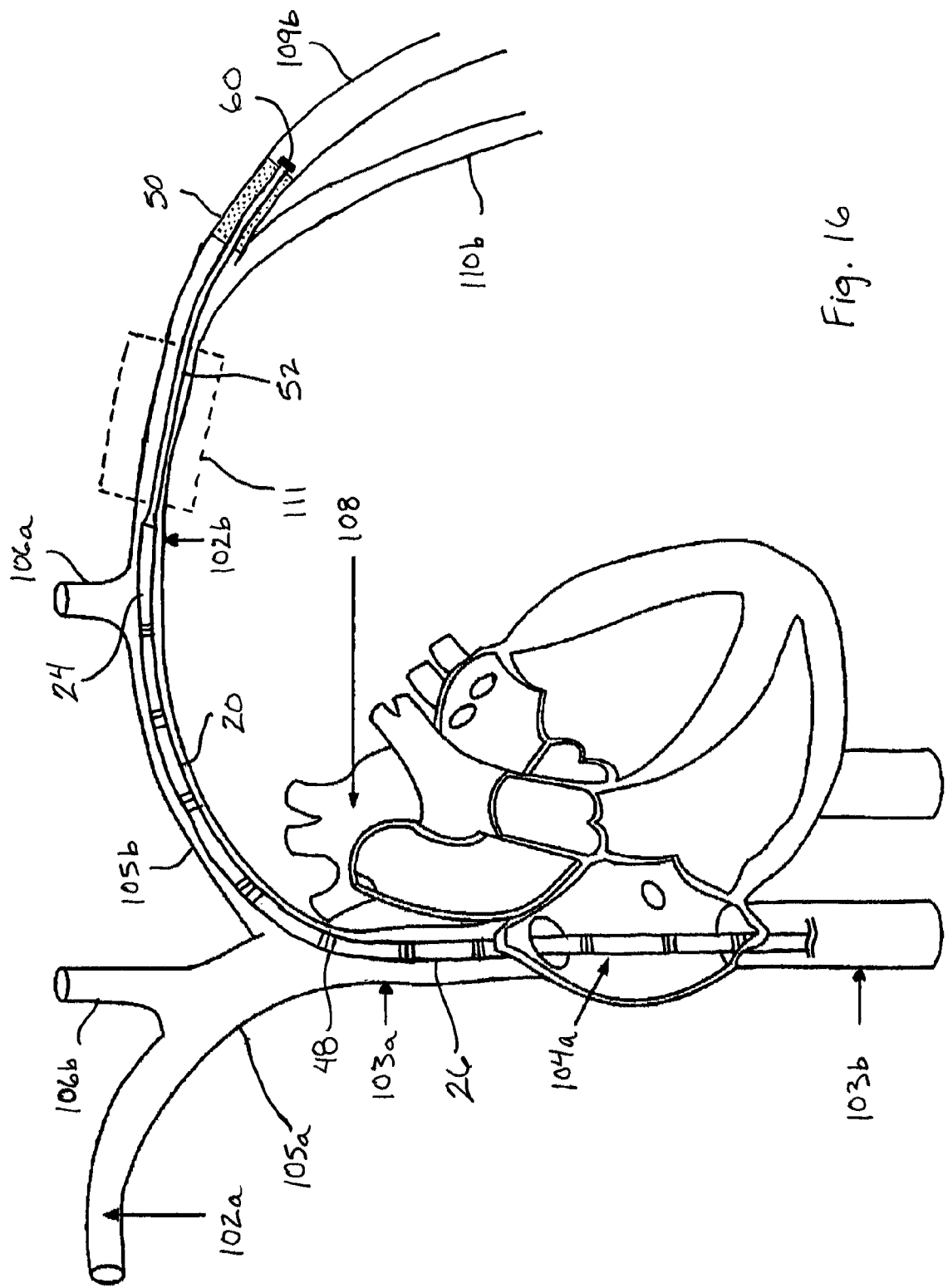
FIG. 16 is a perspective view depicting a further anchor arrangement according to the present invention.

A second suitable superior anchor location is within the right 105a or left 105b cephalic veins, as depicted in FIG. 16. Again, device 20 is generally positioned proximate subclavian crush zone 111, while tether portion 52 extends across and through the crush zone, and into the cephalic vein. Tether portion 52 is secured with an anchor 50 in the cephalic vein.

It should be pointed out that many of the device configurations, components, retention devices and methods, implantation methods and other features are equally suitable for use with other forms of intravascular implants. Such implants might include, for example, implantable neurostimulators, artificial pancreas implants, diagnostic implants with sensors that gather data such as properties of the patient's blood (e.g. blood glucose level) and/or devices that deliver drugs or other therapies into the blood from within a blood vessel.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An intravascular device comprising: an elongate device body with a proximal end and a proximal portion proximate the proximal end and a distal end that is adapted for chronic implantation within vasculature of a patient and that includes a distal portion of the intravascular device proximate the distal end of the elongate device body, wherein the intravascular device comprises an intravascular pulse generator device and further includes at least one lead having at least one electrode thereon extending from the proximal portion of the elongate device body with a free end of the lead adapted to be positioned proximate a chamber of the heart; and an anchor that is radially expandable and is adapted to anchor only the distal portion of the intravascular device within a target vessel located superior to a heart of the patient, such that the proximal portion of the elongate device body is left mechanically unsecured within the vasculature of the patient.

2. The intravascular device of claim 1 wherein the distal portion of the intravascular device has an average cross-sectional diameter that is smaller than an average cross-sectional diameter of the elongate device body other than the distal portion.

3. The intravascular device of claim 1 wherein the distal portion of the intravascular device is a tether portion that extends beyond the distal end of the elongate device body, wherein the target vessel is located beyond a subclavian crush zone of the patient in a direction away from the heart and wherein the tether portion is adapted to be intervascularily positioned in the target vessel without the elongate device body being advanced into the subclavian crush zone.

4. The intravascular device of claim 1 wherein the distal portion includes a tether portion extending beyond the distal end of the device body, the tether portion including structure that interfaces with structure on the anchor to mechanically engage the tether portion with the anchor.

5. The intravascular device of claim 4 wherein the tether portion includes a cleat having a pair of laterally opposed structures on the tether portion, either of which are adapted to interface with structure on the anchor.

6. The intravascular device of claim 5 wherein the cleat includes a pair of laterally opposed clip structures and a corresponding pair of laterally opposed fin structures orthogonally offset from an orientation of the clip structures, wherein the anchor is a radially expandable stent having a plurality of struts that define vertices at intersections thereof, such that when the device body is rotated the fin structures orient one of the clip structures to interface with one of the vertices of the plurality of struts whereby the one of the clip structures engages with the one of the vertices of the plurality of struts when the device body is pulled back relative to the anchor.

7. The intravascular device of claim 1 wherein the device body has an aspect ratio of a cross-sectional diameter to a longitudinal length of less than 1:10.

8. The intravascular device of claim 1 wherein the device body comprises a plurality of generally rigid segments interconnected by a flexible zone, and wherein an aspect ratio of a cross-sectional diameter of a segment to a longitudinal length of a segment is less than 1.5:2.

9. A method of implanting an intravascular device, comprising:

providing an intravascular device having an elongate device body with a proximal end and a proximal portion proximate the proximal end and a distal end that is adapted for chronic implantation within vasculature of a patient and that includes a distal portion of the intravascular device proximate the distal end of the elongate device body the intravascular device including an intravascular pulse generator device having at least one lead having at least one electrode thereon extending from the proximal portion of the elongate device body introducing the intravascular device into the vasculature of the patient;

advancing the intravascular device until the distal portion is positioned within a target vessel superior to a heart of the patient;

anchoring the distal portion of the intravascular device within the target vessel, such that the distal portion of the elongate device body is mechanically secured within the vasculature of the patient while the proximal portion of the elongate device body proximate the proximal end of the elongate device body is left mechanically unsecured within the vasculature of the patient, advancing a free end of the lead to the heart until at least one electrode is positioned proximate a chamber of the heart; and anchoring the lead proximate the free end of the lead.

10. The method of claim 9 wherein advancing the free end of the lead includes positioning the free end of the lead within one of a chamber of the heart or a cardiac vessel of the heart.

11. The method of claim 9 wherein providing the intravascular device provides an intravascular device in which the distal portion is a tether portion that extends beyond the distal end of the elongate device body, wherein the target vessel is located beyond a subclavian crush zone of the patient in a direction away from the heart and advancing the intravascular device further comprises advancing the tether portion to the target vessel without advancing the elongate device body into the subclavian crush zone.

12. The method of claim 9 wherein the target vessel is located superior to the heart and still generally within the torso of the patient, and wherein advancing the intravascular device further comprises advancing the distal portion of the intravascular device to one of the right or left cephalic veins, the right or left innominate (brachiocephalic) veins or the right or left subclavian veins.

* * * * *